United States Patent [19]
Park et al.

[11] Patent Number: 5,518,893
[45] Date of Patent: May 21, 1996

[54] QUICK BIOCHEMICAL OXYGEN DEMAND TEST AND APPARATUS FOR THE SAME

[75] Inventors: Yong-Seok Park; Hyung-Charn Kim; Sung-Hong Kim; Yong-Taek Yi, all of Taejon, Rep. of Korea

[73] Assignee: Yukong Limited, Rep. of Korea

[21] Appl. No.: 212,633

[22] Filed: Mar. 11, 1994

[30] Foreign Application Priority Data

Apr. 16, 1993 [KR] Rep. of Korea .................. 93-6458

[51] Int. Cl.⁶ .................. C12Q 1/02; G01N 21/00
[52] U.S. Cl. .................. 435/29; 435/4; 435/34; 435/817; 435/818; 436/62; 436/138; 436/810; 422/58; 422/79; 422/102; 422/111
[58] Field of Search .................. 435/29, 4, 34, 435/290, 291, 296, 817, 818; 436/62, 138, 810; 422/58, 79, 102, 111

[56] References Cited

U.S. PATENT DOCUMENTS

| | | | |
|---|---|---|---|
| 3,986,932 | 10/1976 | Brushwyler et al. | 436/62 |
| 4,350,763 | 9/1982 | Suzuki et al. | 435/29 |
| 4,898,829 | 2/1990 | Siepmann et al. | 435/289 |

FOREIGN PATENT DOCUMENTS 2952343  12/1979  Germany.
3111759  9/1989  Japan.

OTHER PUBLICATIONS

Kulis et al., *Biological Abstracts*, vol. 75, No. 7, Ref. No. 48697, 1981.

Hyun et al, Biotechnology and Bioengineering, vol. 41, No. 11, pp. 1107–1111, May 1993.

*Primary Examiner*—Michael G. Wityshyn
*Assistant Examiner*—Abdel A. Mohamed
*Attorney, Agent, or Firm*—Seidel Gonda Lavorgna & Monaco

[57] ABSTRACT

The biochemical oxygen demand (BOD) of aqueous liquids containing organic matter is determined. A microorganism culture is aerated to exhaust the organic matter available to the microorganisms. An aqueous liquid test sample containing organic matter is added to the exhausted culture to measure the amount of oxygen consumed by the microorganisms. The determination of biochemical oxygen demand (BOD) of the sample is determined in as little as 20 minutes. An apparatus is provided for determining BOD comprising a magnetic stirrer, an aerating instrument, a dissolved oxygen/temperature sensor, tubing pumps and a quick biochemical oxygen demand (QBOD) bottle. The BOD may be automatically calculated using the apparatus.

4 Claims, 4 Drawing Sheets

QUICK BIOCHEMICAL OXYGEN DEMAND TEST AND APPARATUS FOR THE SAME

BACKGROUND OF THE INVENTION

1. Field of the Invention

The present invention relates in general to a novel method for the determination of biochemical oxygen demand in aqueous liquids containing organic matter and an apparatus for the same, and more particularly to improvements in quickness and accuracy with the method and the apparatus.

2. Description of the Prior Art

Generally, biochemical oxygen demand (hereinafter "BOD") of an aqueous liquid contaminated with organic matter, which is defined as an amount of dissolved oxygen necessary to the metabolic activity of the microorganisms that oxidize the biologically decomposable organic matter to grow, is used as an index that reflects the state of water contamination. BOD is of great importance in industrial working locations. For example, when carrying out a biological process for waste water treatment, the BOD values of influent and in the aeration basin are important parameters in operating the process normally, and in preventing a variety of problems. In addition, since the BOD of effluent is regulated below a legal limit, waste manager always measures the value of BOD to control the effluent quality.

While several quick methods were suggested for the determination of BOD, it is still common practice to measure BOD by Standard Method No. 219 of the American Public Health Association, or by the very similar method of Japanese Industrial Standard JIS K0102-1974. Both methods, however, require a test solution to be held under prescribed conditions for five days before the result of the test can be known. Particularly, the five days is based on the fact that it takes a long time for aerobic microorganisms to grow after a sample is added into a dilute aqueous liquid saturated with oxygen. Thus, BOD measured by the conventional method, in which five days is required to perform the test, is represented as $BOD_5$. What is worse, the conventional method includes another problem in that the value of the test results depends on the skill of the operator. This is because the conventional test is very complicated and intricate. Hence, the above conventional methods are not convenient to control effluent from industrial plants and the like, which requires quickness and accuracy.

One prior art proposal for reducing the test period to, for example, 30 minutes, was disclosed in U.S. Pat. No. 4,350,763 to Shuichi Suzuki at el. issued on 1982 (hereinafter "763' patent"). This method suggests that a sample solution comes into contact with elementary oxygen and with immobilized microorganisms capable of aerobically metabolizing organic matter in an aqueous liquid, thereby consuming the oxygen. In the 763' patent, an adequate number of microorganisms are immobilized to establish the oxygen-consuming ability of the immobilized cells when in contact with solutions having known BOD. The rate of oxygen consumption of the same microorganisms in contact with an unknown test sample is compared with a calibration chart derived from tests on known standard samples. That is, the 763' patent makes use of the principle that the rate of oxygen consumption is directly proportional to the BOD, so that a plot of BOD vs rate of oxygen consumption is represented by a straight line in a system of Cartesian coordinates. For example, microorganisms which are immobilized in a membrane connected with an electrode come into contact with oxygen-saturated buffer free of oxidizable organic matter, in order to establish a constant current indicative of a reference dissolved oxygen (hereinafter "DO"). And when the oxygen-sensitive electrode is immersed in waste water or the like which contains molecular oxygen, the oxygen content of this sample solution is sensed by the electrode. As the immobilized microorganisms metabolize the organic material in the waste water, a resulting variation in the output current of the electrode is obtained. The method utilizing the oxygen-sensitive electrode proposed in 763' patent is advantageous in many aspects, such as quickness, simplicity, and accuracy, as compared with the conventional $BOD_5$.

However, the method of the 763' patent has disadvantages as follows. First, if the number of the microorganisms immobilized in the membrane is not constant, the rates of oxygen consumption are different in respective test case for even the same waste water. Hence wrong BOD results are obtained. Second, a standard curve is necessary to plot a calibration chart, which results from indirect determination of BOD, so that another standard curve is drawn again, depending on the activity variation of the microorganisms. Third, if some constituents of the organic matter do not pass through a general bio-degradation pathway, BOD values thereof are impossible to measure, or may be lower than the real values.

SUMMARY OF THE INVENTION

For solving the aforementioned problems, the inventors have recognized that there exists a need for a faster test less sensitive to human error, which dispenses with a standard curve, and which is indifferent to the bio-degradation pathway of organic matter.

Accordingly, in an aspect of the present invention, there is provided a method for determining the BOD of aqueous liquids containing organic matter, whereby a BOD result can be obtained much faster than conventional methods, normally within less than 20 minutes.

According to another aspect of the present invention, there is provided a method for determining BOD which is less sensitive to the operator's skill.

According to a further aspect of the present invention, there is provided a method for determining BOD, which dispenses with the need for a standard curve.

According to yet another aspect of the present invention, there is provided a method for determining BOD, applicable to any aqueous liquid containing organic matter, even matter under unusual bio-degradation pathways.

According to another aspect of the present invention, there is provided an apparatus for performing the method.

In accordance with the present invention, the above objects can be accomplished by providing a method for determining BOD in an aqueous liquid containing organic matter, comprising the steps of aerating a microorganism culture to exhaust the soluble organic matter completely; adding a sample solution containing the organic matter into the exhausted culture; and measuring the amount of oxygen consumption to determine BOD of the sample directly.

The above objects can be also achieved by providing an apparatus for determining the BOD of an aqueous liquid containing organic matter, which comprises a magnetic stirrer, a quick biochemical oxygen demand (hereinafter "QBOD") bottle provided with a hole for a DO/temperature sensor connected to a recording instrument and with a protruded feed hole, an aerating instrument providing air to a microorganism culture container through an air stone, a tubing pump transferring the microorganism culture from the tank to the QBOD bottle, and another tubing pump draining the microorganism culture from the QBOD bottle.

BRIEF DESCRIPTION OF THE DRAWINGS

The above and other objects, features and advantages of the present invention will be more apparent from the following detailed description taken with reference to the accompanying drawings, in which.

DETAILED DESCRIPTION OF THE INVENTION

The preferred embodiment of the present invention will be, in detail, described with reference to the accompanying drawings.

Figures 1A, 1B:
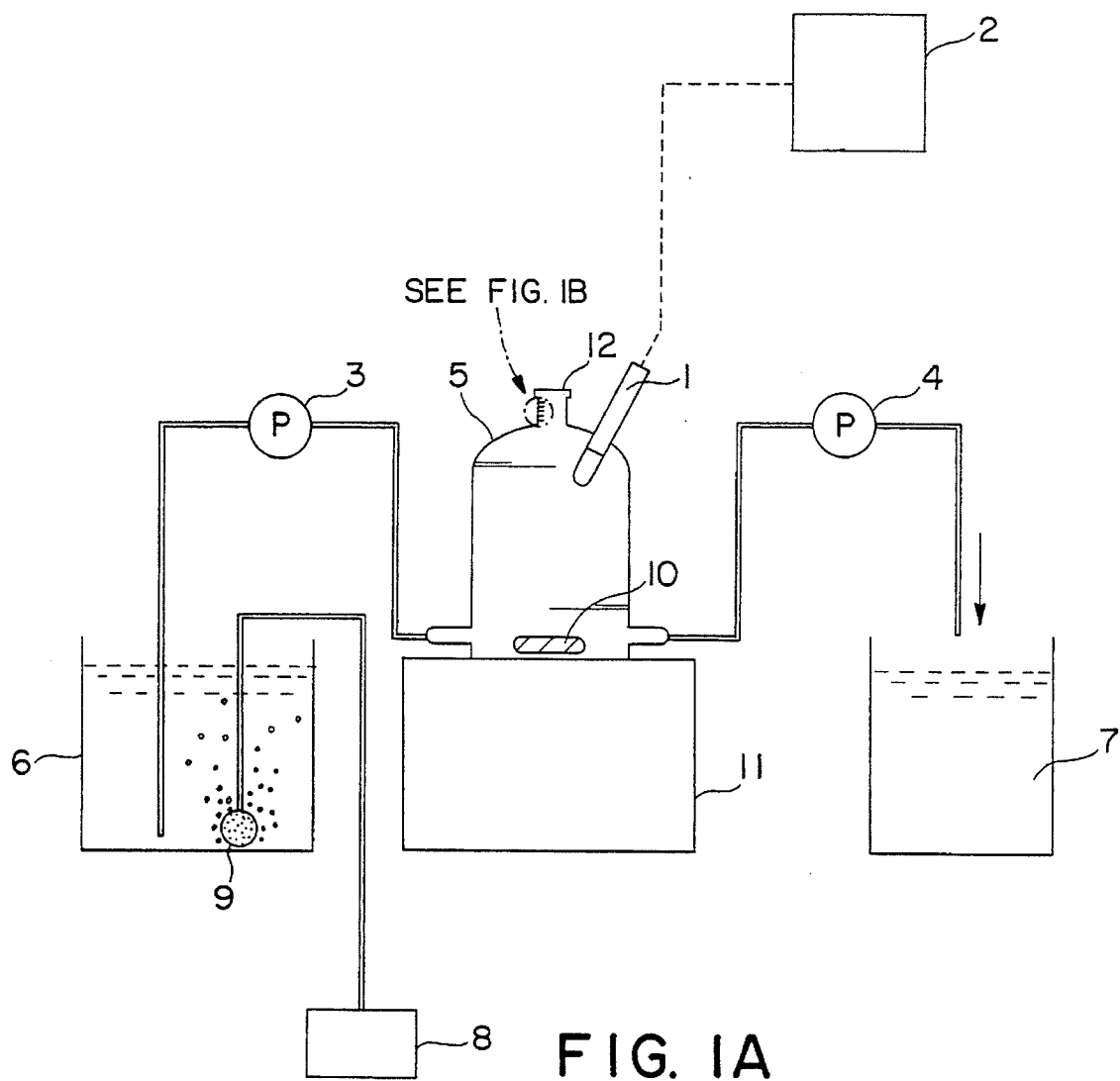
FIG. 1 is a flow sheet of an apparatus suitable for performing the method of the present invention.

Referring to FIG. 1, there is shown an apparatus comprising a QBOD bottle 5 having an opening in which a DO/temperature sensor 1 connected to a recording instrument 2 is obliquely installed, two tubing pumps 3 and 4 connected with the QBOD bottle so as to deliver microorganism cultures from microorganism culture tank 6 and a container 7, an aerating instrument 8 providing air through an air stone 9 to the tank 6, and a magnetic stirrer 11 supporting the QBOD bottle 5 and operating a magnetic bar 10 in the bottle. To operate the QBOD system illustrated in FIG. 1, a microorganism culture such as a solution of an aeration basin, a return sludge and an artificial culture are contained in the tank 9 which is then aerated through the air stone by the aerating instrument 8. The organic matter which is usable to microorganisms in the culture is exhausted so completely as to maintain a high DO value. That is, air is provided to exhaust the organic matter in the culture until the oxygen uptake rate is below 20 ppm-$O_2$/h. The resulting culture is introduced into the QBOD bottle 5 by a tubing pump 3 in such a way to fill upto a neck in the bottle having a scale notched therein. Thereafter, the culture is stirred with the magnetic bar 10 operating at a constant rate by means of the magnetic stirrer 11, so that DO is consumed in a very slow rate. When a predetermined amount of sample solution containing the organic matter is fed to the QBOD bottle through the feed opening 12, the oxygen is consumed for a few minutes as rapidly as the BOD of the fed organic matter permits. Then the consumption rate reverts to the inherited slow rate. In the above procedure, the total amount of the consumed oxygen is the amount consumed by the microorganisms themselves, and the consumption amount based on the addition of the organic matter. Therefore, the total amount of the consumed oxygen minus the amount consumed by the microorganisms themselves is the BOD of the organic matter. From 10 to 10,000 ppm of BOD is measurable without diluting the sample.

As illustrated above, according to the method of the present invention, the BOD of a sample is capable of being determined directly by exhausting the organic matter of a microorganism culture, adding organic matter to the exhausted culture and measuring the consumed oxygen. Accordingly, the number of the microorganisms influences only the measuring time. It does not affect the BOD results. In accordance with the present invention, BOD is determined directly in total, so that a standard curve is not necessary. There is yet another advantage of the present method, in that the measurable range of BOD is from 10 to 10,000 ppm, and the sample does not require dilution. Furthermore, in case where the method according to the present invention is applied to a waste water treatment plant, BOD values are accurately determined from all aqueous liquids from the treatment influent, from aeration basins and the like. The microorganisms for the test are those that are generated from the plant. Thus, they are adapted to the constituents of the waste water.

As compared with the conventional $BOD_5$, the method according to the present invention has the following advantages. First, the inventive method is much faster than the conventional $BOD_5$ (5 days versus 20 minutes). Second, it is more reproducible, being less dependent on operator's skill. Third, it is unnecessary to maintain a particular sample temperature such as 20° C. Fourth, it allows a much more accurate measurement than the BOD test measurement for standard solutions. Fifth, it is not necessary to inoculate microorganisms in the inventive method. Sixth, the inventive method is not affected by nitrifying bacteria. Seventh, it is not largely affected, even if the dilution water is contaminated with microorganisms. Eighth, the inventive method provides a measurable BOD range of about 10 to 10,000 ppm. Repetition of the test at different dilutions is not necessary.

In an apparatus for performing the QBOD test according to the present invention, as shown in FIG. 1, a 300 mL transparent QBOD bottle 5 has a sensor opening for DO/temperature sensor 1 and a protruding feed opening calibrated at the opening upper portion. The bottle has, at opposite sides of its lower portion, two protrusions which are connected with a microorganism culture tank 6 and a container 7 through tubing pumps 3 and 4, respectively. Any commercially available DO/temperature sensor may be used in the present invention. For example, the DO/temperature sensors manufactured and sold by YSI company, USA or Horiba company, Japan may be used. The DO/temperature sensor senses the DO value of the test sample. The sensor is installed obliquely as shown in FIG. 1 to remove test errors generated by bubbles. The DO/temperature sensor is connected to a recording instrument 2, which records a signal generated by the sensor in response to the DO value. The recorder calculates the consumed amount of oxygen with a programmed calculation method and a timer (not shown), so as to determine BOD. The QBOD bottle 5 is mounted on a magnetic stirrer 11 which includes a magnetic bar 10 which uniformly stirs the solution to be tested. The recording instrument 2 which receives the DO value signals may print the decrements in BOD over time, or may plot a graph of BOD versus time. The microorganism culture in the tank 6 is saturated with air which is delivered by an air pump 8 through an air-stone. Through the tubing pumps 3 and 4 which are connected to the QBOD bottle 5, the saturated culture is introduced to the bottle 5 and the used culture is discharged from the bottle 5. Besides operating the magnetic bar 10, the magnetic stirrer 11 may store in memory the amount of a sample to calculate a dilution, which is subsequently utilized for the calculation of BOD. For example, if 0.5 mL of the sample is inputted into the magnetic stirrer 11, the dilution is calculated to 600 (300/0.5). The dilution value is automatically utilized for the calculation of BOD by means of an equipped operating chip.

EXAMPLE 1

About 1 L of the waste water gathered from the aeration basin of the waste water treatment site of a petrochemical plant was poured into the tank 6 at 25° C. The tank was then saturated with air through an air-stone until the DO value of the waste water was constant. When the DO reached a constant value above 80%, the aerated waste water was introduced into the QBOD bottle 5 so as to fill the bottle up to the neck thereof. The contents were stirred at a medium rate of 600 to 700 rpm by a 1 inch bar. The DO values were recorded every 30 seconds, the point when the DO value was decreased by the microorganisms suspended in the waste water. Methanol solutions of 10, 25, 50, 75, 100, 250, 500, 750 and 1,000 ppm were prepared using methanol of reagent grade.

Figure 2:
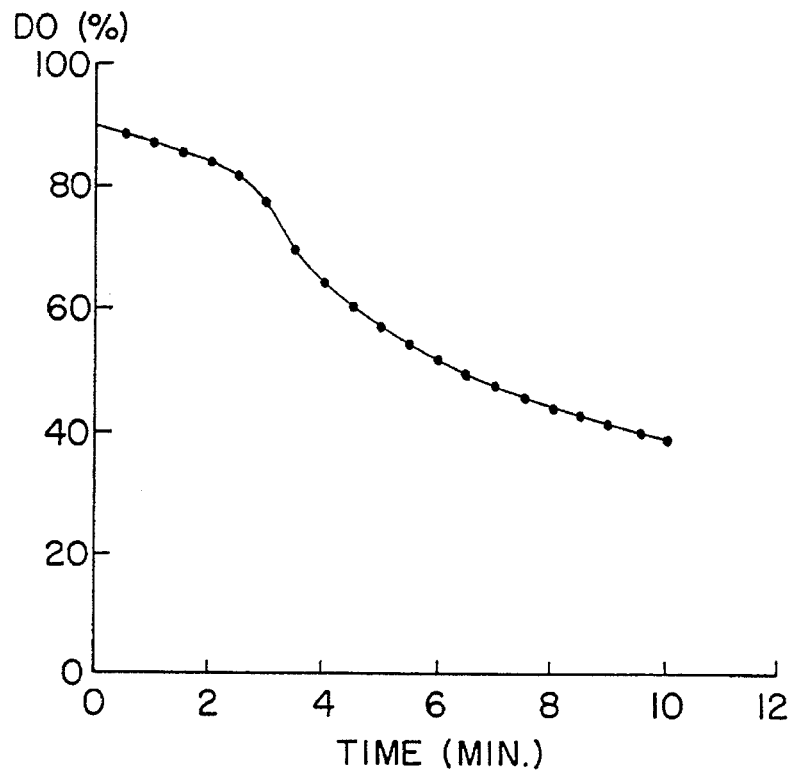
FIG. 2 is a graph illustrating the declination of DO decrease according to Example 1 of the present invention.

When the oxygen uptake rate (OUR) of the microorganisms was constant, 0.5 mL of the 1,000 ppm methanol solution was fed, through a feed hole, into the QBOD bottle. DO values and DO decrements were then measured. The results are given in Table 1 and illustrated in FIGS. 2 and 3.

After feeding the sample, the OUR increased for 8 minutes and returned to the inherited value. At that time, the DO value was 41.3%. During the 8-minute period, the total variation of DO value was 45.7%, which included the inherited amount, 24% (3.0%×8 min.) of oxygen consumed by the microorganisms. As a result, net amount of oxygen consumed by the sample addition was 21.7%. The BOD of the sample is calculated as follows:

$$\text{Sample } BOD = 21.7\% \times \left( \frac{8.3 \text{ ppm}}{100\%} \right) \times \left( \frac{30 \text{ mL}}{0.5 \text{ mL}} \right) = 1,081 \text{ ppm}$$

wherein 8.3 ppm is the oxygen concentration in water at saturation at 25° C.

Figure 3:
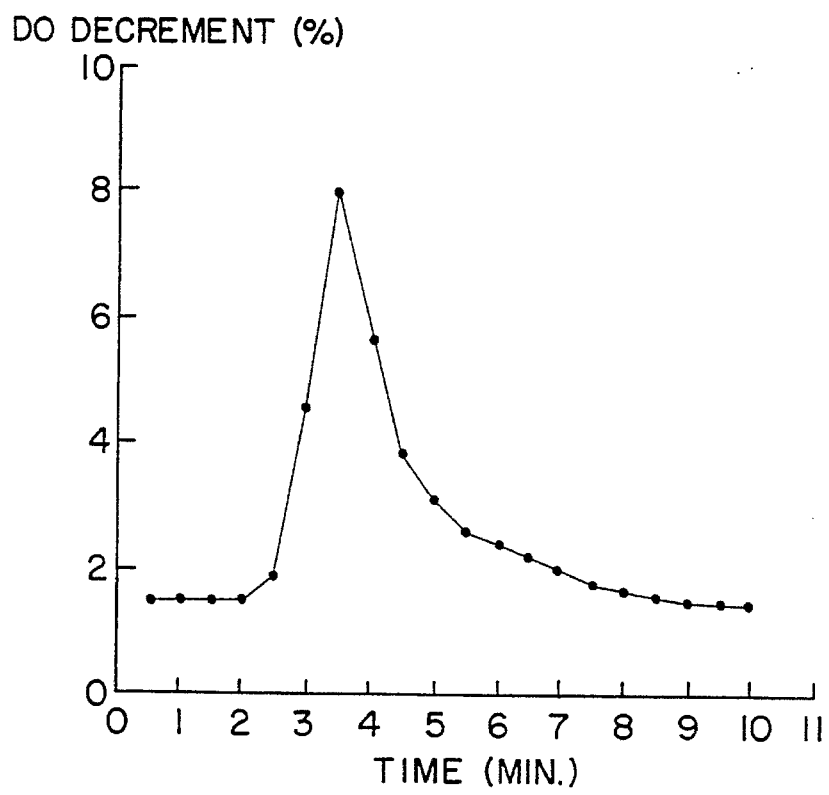
FIG. 3 is a graph illustrating the DO decrements according to Example 1 of the present invention.

The DO values and DO decrements were printed in the QBOD apparatus according to the present invention. The DO decrements over time are shown in FIG. 3. In FIG. 3, the position of the curve ends indicates that the inherited OUR of the microorganisms is 1.5% per 30 seconds. The bell shape of the curve means that the OUR changes depending on the concentration of the organic matter.

The culture used in the QBOD bottle 5 was released into the container 7. Fresh culture from tank 6 was introduced into the bottle 5 because a high DO value was required to determine the BOD of the next sample. During the determination of the BOD, the microorganism culture in the container 7 was poured into the tank 6 and then aerated. Solutions of 100, 250, 500 and 1,000 ppm were tested in a manner similar to that mentioned above. The results were 112, 28, 525 and 803 ppm, respectively. 5 ml of the methanol solutions of 10, 25, 50, 75 and 100 ppm were tested in a similar manner. The results were 11, 27, 59, and 104 ppm, respectively.

Figure 4:
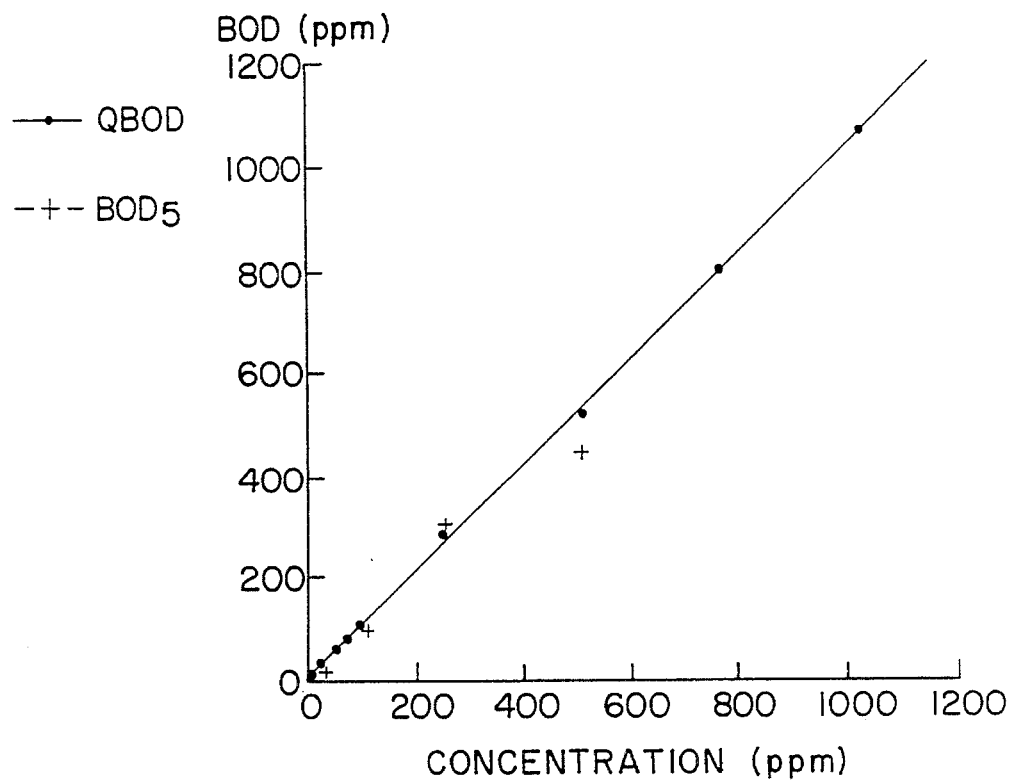
FIG. 4 is a graph illustrating the QBOD and $BOD_5$ with regard to the concentration of the methanol according to Example 1.

$BOD_5$ values were measured for the methanol solutions of 25, 100, 250 and 500 ppm, using a Model 2173B manometer-type BOD measuring apparatus of HACH company, U.S.A. The results were 20, 115, 290 and 450 ppm, respectively. QBOD and $BOD_5$ are plotted in FIG. 4.

EXAMPLE 2

About 1 L of the waste water gathered from the aeration basin of the waste water treatment site of a petrochemical plant was poured into the tank 6 at 25° C. The tank was then saturated with air through an air-stone until the DO value of the waste water was constant. When the DO reached a constant value above 80%, the aerated waste water was introduced into the QBOD bottle 5 so as to fill the bottle up to the neck thereof. The contents were stirred at a medium rate of 600 to 700 rpm by a 1 inch bar. From the point when the DO value was decreased by the microorganisms suspended in the waste water, the values were recorded every 30 seconds. Solutions of 500 ppm acetic acid, ethanol and phenol were prepared.

Figure 5:
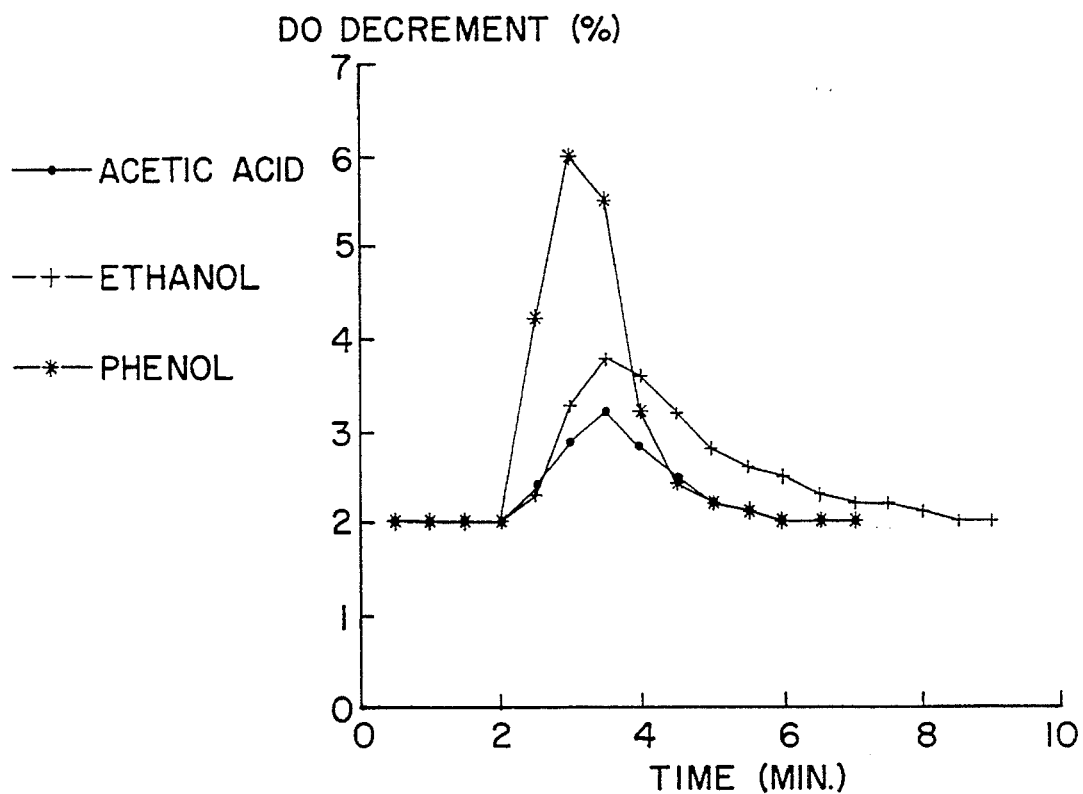
FIG. 5 is a graph illustrating the DO decrements depending on the addition of acetic acid, ethanol and phenol solutions according to Example 2 of the present invention.

When the microorganisms OUR was constant in the QBOD bottle, 0.5 mL of the acetic acid solution was fed through a feed opening into the QBOD bottle. The value "0.5 mL" was inputted into the magnetic stirrer. Within 10 minutes of feeding the sample, the BOD value was shown at a display window on the recording instrument. The test results were 438 and 478 ppm, respectively, for the ethanol and phenol solutions. The DO decrements are printed every 30 seconds in the QBOD apparatus according to the present invention, and were shown in FIG. 5.

$BOD_5$ values were measured for the above three solutions and the results were 220, 445 and 505 ppm, respectively.

Figure 6:
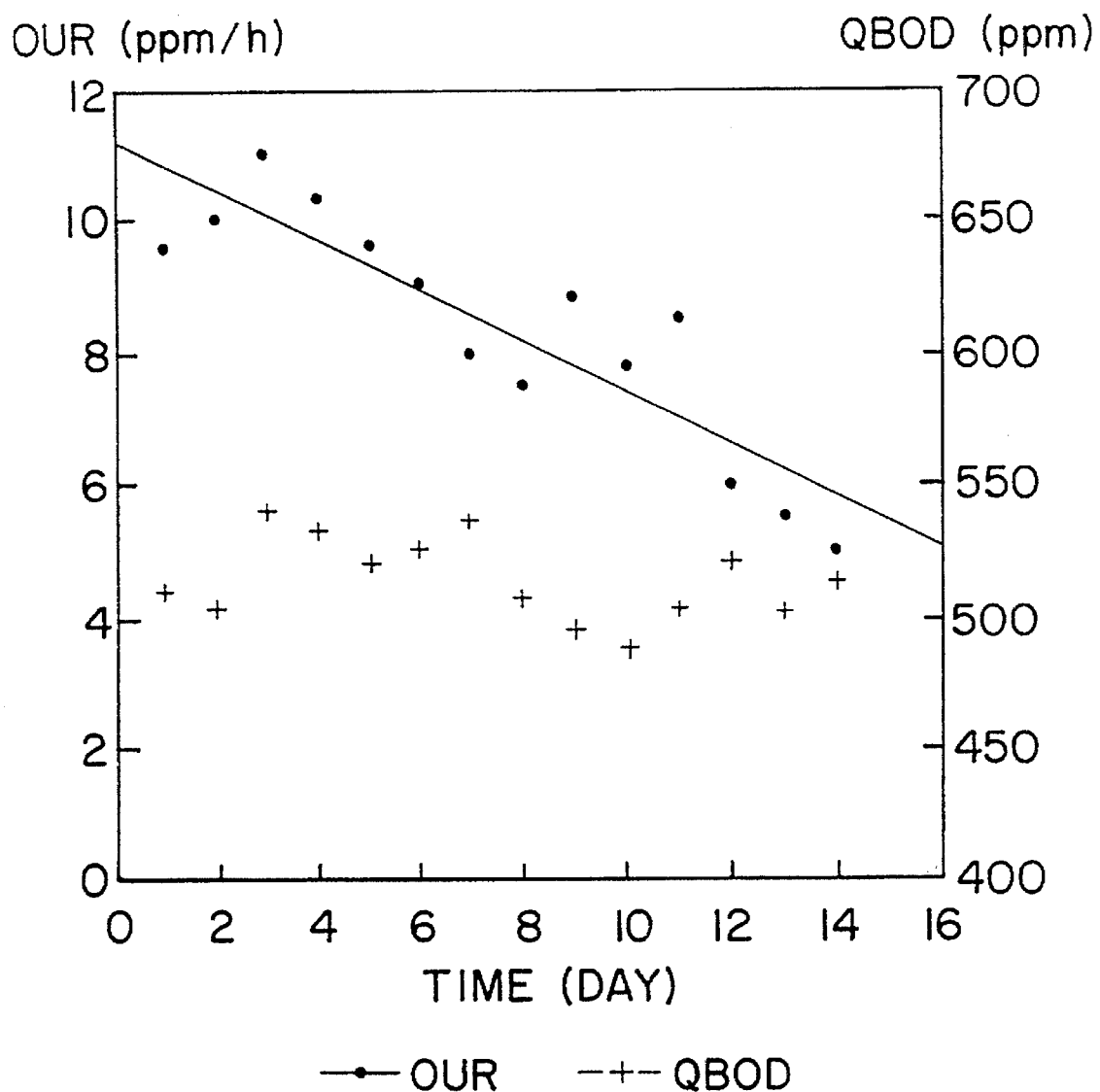
FIG. 6 is a graph illustrating the stability of the microorganism culture according to Example 2 of the present invention.

To test the stability of the microorganism culture with regard to time, the inherited OUR and the QBOD of methanol of 500 ppm were measured. The inherited OUR of a microorganism culture which was maintained at 25° C. decreased over time, as shown in FIG. 6. However, the QBOD value was constant for over 15 days, being indifferent to the inherited OUR. During the 15-day period, the average QBOD value was 514 ppm, and the standard deviation was 16.4. When the BOD of sample was measured with the remaining microorganism culture, the aeration in the tank 6 was operated for not less than 1 hour so as to keep the DO value constant in a state of not less than 80%.

TABLE 1

| | DO variations depending on the addition of MeOH solution | | | | | | |
|---|---|---|---|---|---|---|---|
| Sample Time (min.) | MeOH 1,000 ppm | | | Sample Time (min.) | MeOH 1,000 ppm | | |
| | DO(%) | ΔDO(%) | Remark | | DO(%) | ΔDO(%) | Remark |
| 0 | 90 | | 25° C. | 5.5 | 54.6 | 2.6 | |
| 0.5 | 88.5 | 1.5 | | 6 | 52.1 | 2.4 | |
| 1 | 87.0 | 1.5 | sample add. | 6.5 | 49.9 | 2.2 | |

TABLE 1-continued

DO variations depending on the addition of MeOH solution

| Sample Time (min.) | MeOH 1,000 ppm | | | Sample Time (min.) | MeOH 1,000 ppm | | |
|---|---|---|---|---|---|---|---|
| | DO(%) | ΔDO(%) | Remark | | DO(%) | ΔDO(%) | Remark |
| 1.5 | 85.5 | 1.5 | | 7 | 47.9 | 2.0 | |
| 2 | 84.0 | 1.5 | | 7.5 | 46.1 | 1.8 | |
| 2.5 | 82.1 | 1.9 | | 8 | 44.4 | 1.7 | |
| 3 | 77.6 | 4.5 | | 8.5 | 42.8 | 1.6 | |
| 3.5 | 69.6 | 8.0 | | 9 | 41.3 | 1.5 | finish |
| 4 | 64.0 | 5.6 | | 9.5 | 39.8 | 1.5 | |
| 4.5 | 60.0 | 3.8 | | 10 | 38.3 | 1.5 | 25.1° C. |
| 5 | 57.4 | 3.1 | | | | | |

What is claimed is:

1. In a method for determining the biochemical oxygen demand (BOD) of an aqueous liquid containing organic matter using a culture of microorganisms, in which the liquid contains dissolved oxygen (DO) and microorganisms capable of aerobically metabolizing the organic matter and thereby consuming oxygen in the sample, the improvement comprising the steps of:

(i) aerating a culture of microorganisms gathered from an aeration basin of a waste water treatment site to exhaust the dissolved organic matter in the culture until an exhausted state is achieved wherein the dissolved oxygen (DO) value is constant at a value above 80%;

(ii) introducing said aerated culture into a quick biochemical oxygen demand (QBOD) bottle having a constant volume under stirring with a magnetic stirrer;

(iii) measuring the oxygen uptake ratio (OUR) of the exhausted state at a time when the OUR becomes constant, and measuring the DO value at that time;

(iv) feeding a sample containing the organic matter degradable by the microorganisms into said QBOD bottle, causing the OUR of said culture to increase;

(v) measuring the OUR of said culture fed with organic matter at a time when the OUR reaches a value as low as the OUR value of the exhausted state of step (iii), measuring the DO value of said culture at that time, and measuring the time elapsed (T) for said OUR value to return to said exhausted state value; and (vi) calculating the BOD of the sample by the equation:

wherein $$BOD = A \left( \frac{\text{(volume of sample containing organic material + volume of culture)}}{\text{volume of sample containing organic material}} \right)$$

$$A = [DO_{step(iii)} - DO_{step(v)}] - [OUR_{step(iii)} \times T].$$

2. The method according to claim 1, in which the step of aerating the culture is continued until the oxygen uptake rate of the microorganisms is not more than 20 ppm-$O_2$/h.

3. A method according to claim 1, in which the microorganism culture is selected from the group consisting of a solution from an aerated basin, a return sludge and an artificial microorganism culture.

4. The method according to claim 1, in which the BOD of the sample is measured in a range of from about 10 to about 10,000 ppm, without diluting the sample.

* * * * *